United States Patent [19]

Corty

[11] 4,032,654
[45] June 28, 1977

[54] WATER-SOLUBLE, LIQUID CONCENTRATES OF S-METHYL-[(METHYL-CARBAMOYL)OXY]-THIOACETIMIDATE AND METHYL N', N'-DIMETHYL-N-[(METHYL-CARBAMOYL)OXY]-1-THIOOXAMIMIDATE

[75] Inventor: Claude Corty, Wilmington, Del.

[73] Assignee: E. I. Du Pont de Nemours and Company, Wilmington, Del.

[22] Filed: Nov. 20, 1975

[21] Appl. No.: 633,838

Related U.S. Application Data

[63] Continuation-in-part of Ser. No. 484,308, June 28, 1974, abandoned.

[52] U.S. Cl. .............................. 424/298; 424/173; 424/300; 424/327
[51] Int. Cl.² .......................................... A01N 9/00
[58] Field of Search ........... 424/298, 300, 327, 173

[56] References Cited

UNITED STATES PATENTS

| | | | |
|---|---|---|---|
| 3,530,220 | 9/1970 | Buchanan | 424/320 |
| 3,639,633 | 2/1972 | Buchanan | 424/327 |
| 3,862,316 | 1/1975 | Armstrong | 424/173 |

*Primary Examiner*—Leonard Schenkman

[57] ABSTRACT

Chemically and physically stable insecticidal, nematocidal, water-soluble, liquid concentrates of (a) S-methyl-[(methylcarbamoyl)oxy]-thioacetimidate, and (b) methyl N',N'-dimethyl-N-[(methylcarbamoyl)oxy]-1-thiooxamimidate when dissolved in an appropriate solvent, preferably methanol and water, in the presence of a small amount of acid, display solubility synergism.

7 Claims, 2 Drawing Figures

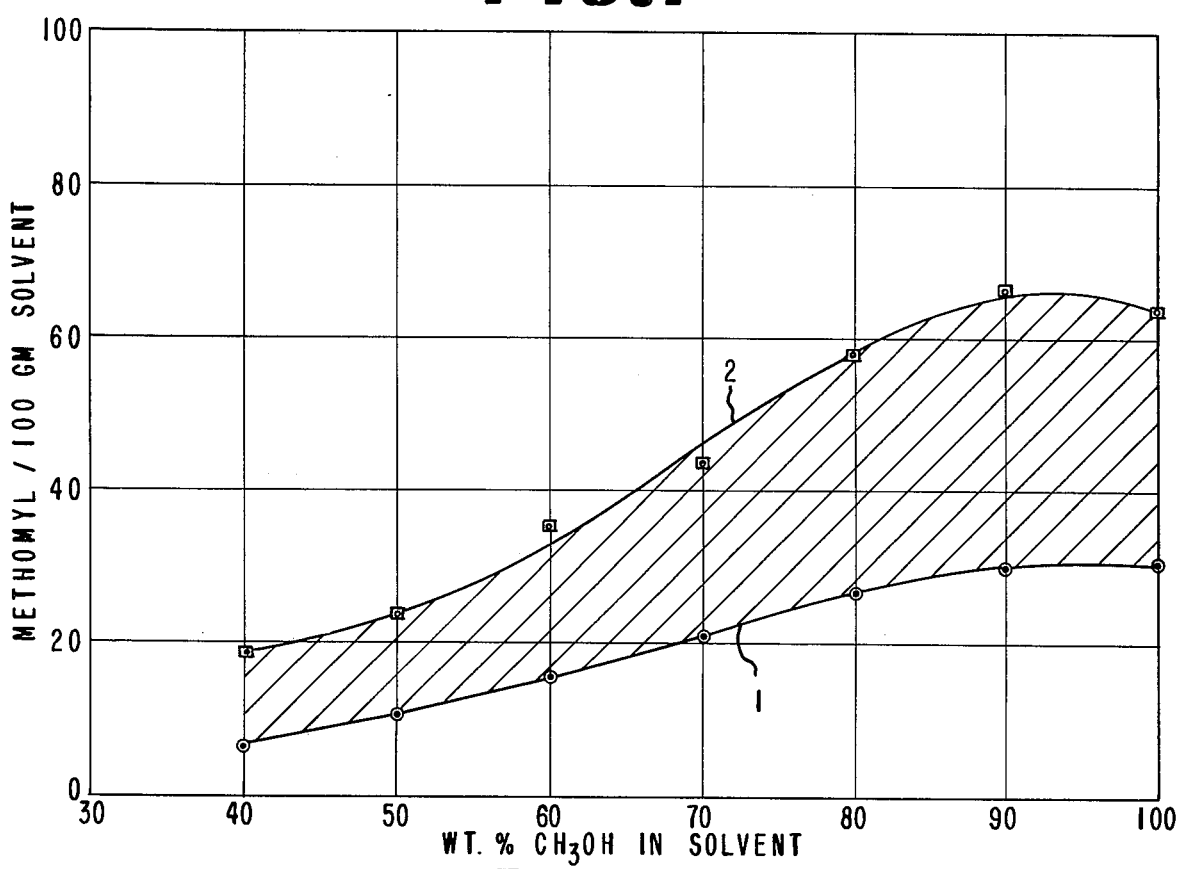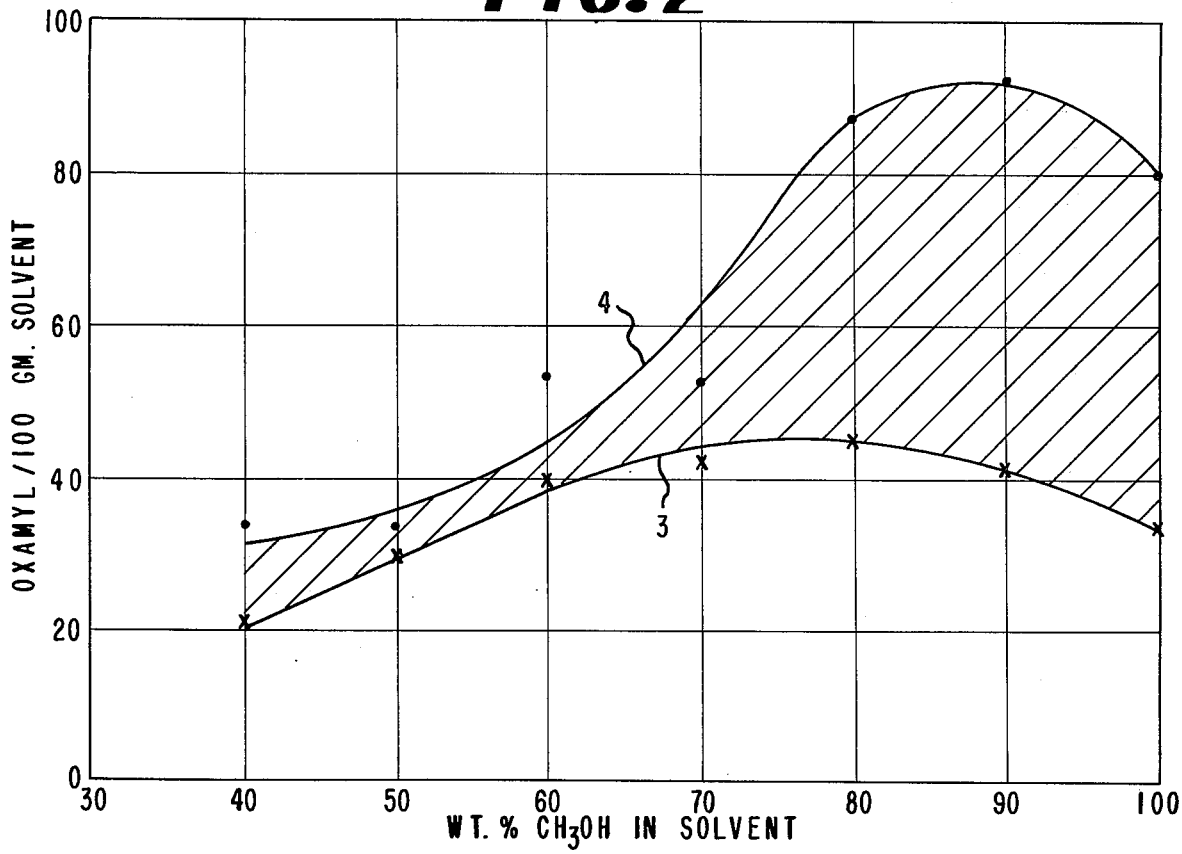

WATER-SOLUBLE, LIQUID CONCENTRATES OF S-METHYL-[(METHYL-CARBAMOYL)OXY]-THIOACETIMIDATE AND METHYL N′,N′-DIMETHYL-N-[(METHYL-CARBAMOYL)OXY]-1-THIOOXAMIMIDATE

CROSS REFERENCE TO RELATED APPLICATION

This application is a continuation-in-part of my co-pending application Ser. No. 484,308, filed June 28, 1974, now abandoned.

BACKGROUND OF THE INVENTION

The use of

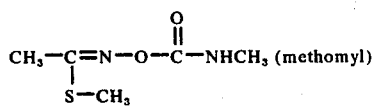

and

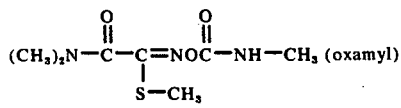

as insecticides and nematocides is well known in the art.

On occasion one may wish to apply these materials together in order to get the benefit of both. In those instances, a single product containing both compounds provides economies of packaging and shipping, makes it more convenient to prepare a spray solution and avoids dosage errors.

It is therefore desirable to maximize the amount of active ingredient, methomyl and oxamyl, which can be transported in a single container.

SUMMARY OF THE INVENTION

According to this invention, methomyl and oxamyl in certain ratios can be dissolved in designated solvents, at a pH of about 2.8–3.2 with the unexpected result that the total amount, expressed as grams of active per 100 grams of solvent, is greater than the total of the amounts of each which could be dissolved separately in the same solvent system.

The initial weight ratios of methomyl to oxamyl to be dissolved to constitute the concentrates of this invention can be from about 2:1 to about 1:2.5. The solvent systems which can be utilized include methanol/water containing from about 0 to 70 weight percent water; acetone/water containing from about 0 to 70 weight percent water; or cyclohexanone/cyclohexanol/methanol/water containing from about 20–92 weight percent cyclohexanone and cyclohexanol provided at least 35% of this component is cyclohexanone, about 3–25 weight percent methanol and at least about 5 weight percent water.

The pH of the system must be acidic and in general sufficient acid is needed to maintain a pH of about 2.8–3.2

Other additives such as colorants may be introduced into the concentrates if desired.

Methomyl and oxamyl may be characterized by the following formulae: S-methyl-[(methylcarbamoyl)oxy]-thioacetimidate (methomyl) and methyl N′,N′-dimethyl-N-[(methylcarbamoyl)oxy]-1-thiooxamimidate (oxamyl).

DETAILED DESCRIPTION OF THE INVENTION

In more detail, the instant invention relates to the unexpected finding that when one combines methomyl and oxamyl in a designated solvent, unexpected solubility synergism is observed. That is to say, when one adds both methomyl and oxamyl, in the designated ratio, to a designated solvent, one is able to dissolve an unexpectedly large amount of total mixed active ingredient in the solvent. Depending upon the lowest temperature which the solution must withstand without crystallization, one can obtain a concentration of 1 to 5 lbs. of total active ingredient per U.S. gallon of solution. The weight ratio of methomyl to oxamyl is about 2:1 to about 1:2.5, preferably about 1.5:1 to 1:1.5 and most preferably about 1:1 to 1:1.5.

The solvents may be a system of methanol/water containing from about 0–70 weight percent water; acetone-water containing from about 0–70 weight percent water; or cyclohexanone/cyclohexanol/methanol/water containing from about 20–92 weight percent cyclohexanone and cyclohexanol provided at least about 35% of this component is cyclohexanone, about 3–25 weight percent methanol and at least about 5% water. The preferred solvent is a system of methanol/water containing from about 0–70 percent water, most preferably about 20–50 percent.

The pH may vary from about 2.8 to 3.2; the most preferred acid to be utilized is phosphoric acid, but other acids such as acetic, citric and sulfuric acid are also acceptable so long as the desired pH is obtained. In a preferred embodiment, phosphoric acid in the amount of about 0.4 to 0.6 weight percent is utilized. If desired, warning agents may be added such as dyes, colorants, or odor-producing chemicals. Typically, a coloring agent would be added in an amount from about 0.01–0.10 percent. Suitable coloring agents would be "Marasperse", a product of the American Can Company, "Lignosols", sold by Lignosol Chemicals Company, or organic dyes such as FD & C Blue No. 1, FD & C Red No. 3 (773 erythrosine) or FD & C Yellow No. 5 (640 tartrazine). In fact, any coloring agents that do not react chemically with the other formulation ingredients may be utilized. Combinations of coloring agents are also suitable. "Marasperse" CB, or FD & C Blue No. 1 are the preferred coloring agent.

The preparation of both methomyl and oxamyl is well known to one skilled in the art. For instance, the preparation of methomyl and its various uses as an insecticide, nematocide etc. are included in U.S. Pat. No. 3,639,633 to James B. Buchanan, the disclosure of which is herein incorporated by reference. The preparation of oxamyl and its uses for various purposes such as an insecticide, miticide, or nematocide are taught in U.S. Pat. No. 3,530,220 to Buchanan, the disclosure of which is herein incorporated by reference.

As would be expected, the concentrates of the instant invention are useful for controlling insects, other arthropod pests and pestiferous mollusks and nematodes.

The methomyl, oxamyl, acid and any other ingredients such as coloring agents may be mixed in conventional equipment by conventional means. For instance, they may be mixed as follows: The solvent system and acid are added to a glass-lined or stainless steel kettle equipped with a stirring mechanism and facilities for blanketing the kettle with nitrogen or other inert gas to reduce the fire hazard of the flammable solvents. The active ingredients and the warning agent such as a coloring agent are added to the kettle while stirring; stirring is continued until the active ingredients and coloring agent are dissolved. The solution can then be filtered by techniques known in the art. A "sparkler" filter may be used.

at a concentration exceeding the solubility limit at $-6°$ C. Each sample was seeded with methomyl and/or oxamyl at $-6°$ C and allowed to crystallize until equilibrium was established. The supernatant liquid of each sample was assayed for methomyl and/or oxamyl by liquid chromatography. The following results were obtained.

SOLUBILITY OF METHOMYL AND OXAMYL (1:1 WT. RATIO)
IN $CH_3OH/H_2O$ AT $-6°$ C IN GMS/100 GMS SOLVENT

| Solvent %$CH_3OH$/%$H_2O$ | Both Actives in Solvent | | | Methomyl Alone in Solvent gms | Oxamyl Alone in Solvent gms |
|---|---|---|---|---|---|
| | Methomyl gms | Oxamyl gms | Methomyl & Oxamyl gms | | |
| 100/0 | 63.9 | 80 | 143.9 | 30.7 | 33.3 |
| 90/10 | 66.4 | 92.0 | 158.4 | 29.9 | 40.6 |
| 80/20 | 58.1 | 87.0 | 145.1 | 26.3 | 44.7 |
| 70/30 | 43.8 | 52.7 | 96.5 | 20.8 | 42.2 |
| 60/40 | 35.5 | 53.2 | 88.7 | 15.5 | 39.7 |
| 50/50 | 23.7 | 33.3 | 57.0 | 10.5 | 29.0 |
| 40/60 | 18.8 | 33.7 | 52.5 | 6.2 | 20.9 |

EXAMPLE 1

Formulations of the following compositions are prepared by dissolving the methomyl, oxamyl and coloring agent, where applicable, in the solvent system and acid at ambient temperature. The solution is clarified by filtration techniques known in the art.

| A. | methomyl | 22 lb. |
|---|---|---|
| | oxamyl | 22 lb. |
| | "Marasperse" CB[1] | 0.025 lb. |
| | $CH_3OH$ | 33.3 lb. |
| | $H_2O$ | 22.1 lb. |
| | 85% $H_3PO_4$ | 0.33 lb. |
| B. | methomyl | 20 lb. |
| | oxamyl | 10 lb. |
| | F.D. & C. Blue No. 1[2] | 0.01 lb. |
| | $CH_3OH$ | 62.7 lb. |
| | $H_2O$ | 6.9 lb. |
| | 85% $H_3PO_4$ | 0.33 lb. |
| C. | methomyl | 15 lb. |
| | oxamyl | 15 lb. |
| | acetone | 52 lb. |
| | water | 13 lb. |
| | 85% $H_3PO_4$ | 5 lb. |
| D. | methomyl | 20 lb. |
| | oxamyl | 30 lb. |
| | cyclohexanone | 27 lb. |
| | $CH_3OH$ | 4.5 lb. |
| | water | 13.5 lb. |
| | 85% $H_3PO_4$ | 5 lb. |
| E. | methomyl | 15 lb. |
| | oxamyl | 15 lb. |
| | cyclohexanone | 15.6 lb. |
| | cyclohexanol | 19.5 lb. |
| | $CH_3OH$ | 9.75 lb. |
| | water | 20.15 lb. |
| | 85% $H_3PO_4$ | 5 lb. |

[1] Available from American Can Co.
[2] Available from H. Kohnstamm & Co. Inc., New York or Chicago.

EXAMPLE 2

Methomyl and oxamyl were added to various methanol:water solvent systems ranging from 100% $CH_3OH$ to 40% $CH_3OH$:60% $H_2O$. The methomyl and oxamyl were dissolved separately or combined on a 1:1 weight ratio in the solvent systems at room temperature The table illustrates that in a common solution, both the total combined amount of actives as well as the amount of each individual component has been increased over what a solution of each active ingredient alone in that solvent could contain.

The following figures plot the solubility data of Example 2. Curve 1 of FIG. 1 plots the solubility of methomyl alone in the various methanol/water solvents. Curve 2 of FIG. 1 plots the solubility of methomyl in the presence of oxamyl. Curve 3 of FIG. 2 plots the solubility of oxamyl alone in the various methanol/water solvents. Curve 4 of FIG. 2 plots the solubility of oxamyl in the presence of methomyl. The shaded areas between curves 1 and 2 and between curves 3 and 4 represent the increase in solubility derived from having both methomyl and oxamyl present.

EXAMPLE 3

Solubility of Methomyl and Oxamyl (2:1 wt. ratio) in $CH_3OH/H_2O$ at $-6°$ C

Methomyl and oxamyl were added to various methanol:water solvent systems ranging from 100 wt. % $CH_3OH$ to 30 wt. % $CH_3OH$:70 wt. % $H_2O$. The methomyl and oxamyl were dissolved in a 2:1 weight ratio of 50 wt. % methomyl to 25 wt. % oxamyl in the solvent systems. The samples were equilibrated at $-6°$ C in a constant temperature freezer after which they were seeded with methomyl and oxamyl crystals to ensure crystallization of both materials. After crystal-liquid equilibrium was assured, liquid was removed at $-6°$ C and assayed for methomyl and oxamyl. Solids were also removed at $-6°$ C, washed with hexane and dried. The solids were then dissolved in methanol to yield a 10 wt. % solution. This solution was evaluated by thin layer chromatography (TLC) to ensure the solids consisted of both methomyl and oxamyl. All solids were composed of the mixture. The following assays were obtained on the liquids.

| SOLUBILITY OF METHOMYL AND OXAMYL (2:1 WT. RATIO) IN CH₃OH/H₂O AT −6° C IN GMS/100 GMS SOLVENT | | | | | |
|---|---|---|---|---|---|
| Solvent | Both Actives in Solvent | | | Methomyl Alone in | Oxamyl Alone |
| %CH₃OH/%H₂O | Methomyl gms | Oxamyl gms | Methomyl & Oxamyl gms | Solvent gms | Solvent gms |
| 100/0 | 82.5 | 113 | 195.5 | 30.7 | 33.3 |
| 90/10/ 73.7 | 106 | 179.7 | 29.9 | 40.6 | |
| 80/20 | 59.8 | 94.7 | 154.5 | 26.3 | 44.7 |
| 70/30 | 34.2 | 89.1 | 123.3 | 20.8 | 42.2 |
| 60/40 | 55.2 | 99.2 | 154.4 | 15.5 | 39.7 |
| 50/50 | 46.1 | 96.6 | 142.7 | 10.5 | 29.0 |
| 40/60 | 42.2 | 100 | 142.2 | 6.2 | 20.9 |
| 30/70 | 24.1 | 57.4 | 81.5 | — | — |

The above data illustrate that the solubility of both methomyl and oxamyl is increased in methanol:water solvent systems when a 2:1 wt. ratio of methomyl to oxamyl is dissolved initially. Furthermore, the total amount of active ingredient in a given solution, when both oxamyl and methomyl are present in combination in solution is much greater than the sum of the individual components dissolved in separate solutions. In addition, the quantity of solvent needed to dissolve given quantities of oxamyl and methomyl when in mixture is less than ⅓ the quantity of solvent needed to dissolve the oxamyl and methomyl individually.

EXAMPLE 4

Solubility of Methomyl and Oxamyl 1:2.5 wt. ratio in CH₃OH:H₂O at −6° C

Example 3 was repeated by dissolving methomyl and oxamyl in a 1:2.5 weight ratio in the same solvent systems under the same conditions. The following methomyl and oxamyl solubilities at −6° C were found. TLC indicated the solids in each sample contained both materials.

| SOLUBILITY OF METHOMYL AND OXAMYL (1:2.5 WT. RATIO) IN CH₃OH/H₂O AT −6° C IN GMS/100 GMS SOLVENT | | | | | |
|---|---|---|---|---|---|
| Solvent | Both Actives in Solvent | | | Methomyl Alone in | Oxamyl Alone in |
| %CH₃OH/%H₂O | Methomyl gms | Oxamyl gms | Methomyl & Oxamyl gms | Solvent gms | Solvent gms |
| 100/0 | 71.1 | 72.3 | 143.4 | 30.7 | 33.3 |
| 90/10 | 69.9 | 76.4 | 146.3 | 29.9 | 40.4 |
| 80/20 | 57.3 | 73.7 | 131.0 | 26.3 | 44.8 |
| 70/30 | 22.0 | 46.1 | 68.1 | 20.6 | 42.3 |
| 60/40 | 44.0 | 74.8 | 118.8 | 15.5 | 39.6 |
| 50/50 | 41.1 | 74.0 | 115.1 | 10.5 | 29.1 |
| 40/60 | 28.8 | 51.6 | 80.4 | 6.2 | 20.9 |
| 30/70 | 15.6 | 34.7 | 50.3 | — | — |

EXAMPLE 5

Methomyl and/or oxamyl were added to a solvent system consisting of 60% cyclohexanone, 10% methanol and 30% water at room temperature at a concentration higher than the solubility limit at −6° C. The methomyl and oxamyl were added together, at weight ratios of 2:1, 1:1 and 1:2.5. The solutions were cooled to −6° C and seeded with methomyl and/or oxamyl to initiate crystallization. The solutions remained at −6° C until equilibrium was assured. The supernatant liquid in each sample was analyzed for methomyl and oxamyl by liquid chromatography. The following results were obtained.

| SOLUBILITY OF METHOMYL AND OXAMYL (2:1, 1:1 and 1:2.5 WT. RATIOS) IN CYCLOHEXANONE, CH₃OH AND H₂O AT −6° C IN GMS/100 GMS SOLVENT | | | | | |
|---|---|---|---|---|---|
| Methomyl/Oxamyl ratio | Both Actives in Solvent | | | Methomyl Alone in | Oxamyl Alone in |
| | Methomyl gms | Oxamyl gms | Methomyl & Oxamyl gms | Solvent gms | Solvent gms |
| 2:1 | 64.8 | 84.8 | 149.6 | 29.5 | 48.4 |
| 1:1 | 46.2 | 80.1 | 126.3 | 29.5 | 48.4 |
| 1:2.5 | 66.6 | 82.7 | 149.3 | 29.5 | 48.4 |

EXAMPLE 6

Methomyl and Oxamyl Solubility In Cyclohexanone, Cyclohexanol, CH₃OH and H₂O at −6° C Methomyl and oxamyl were dissolved separately and in weight ratios of 1:1, 2:1 and 1:2.5 methomyl to oxamyl in a solvent system consisting of 30 wt. % cyclohexanone, 30 wt. % cyclohexanol, 30 wt. % water and 10 wt. % methanol. These solutions were equilibrated at −6° C and seeded with methomyl and/or oxamyl crystals. The samples of liquid and solids remained at −6° C until solid-liquid equilibrium was assured. A liquid sample was removed from each at −6° C and assayed for methomyl and/or oxamyl. Solids were also isolated at −6° C, washed, dried and dissolved in CH₃OH to yield a 10% solution which was analyzed by TLC to ensure both methomyl and oxamyl crystals were present in the solids of the combination sample. All such solids contained both oxamyl and methomyl.

SOLUBILITY OF METHOMYL AND OXAMYL (2:1, 1:1 and 1:2.5 Wt. RATIOS) IN CYCLOHEXANONE, CYCLOHEXANOL, CH₃OH AND H₂O AT −6° C IN GMS/100 GMS SOLVENT

| Methomyl/Oxamyl ratio | Both Actives in Solvent | | | Methomyl Alone in Solvent gms | Oxamyl Alone in Solvent gms |
|---|---|---|---|---|---|
| | Methomyl gms | Oxamyl gms | Methomyl & Oxamyl gms | | |
| 2:1 | 42.7 | 83.0 | 125.7 | 24.5 | 41.5 |
| 1:1 | 39.6 | 63.7 | 103.3 | 24.5 | 41.5 |
| 1:2.5 | 40.2 | 61.8 | 102.0 | 24.5 | 41.5 |

EXAMPLE 7

Solubility of Methomyl and Oxamyl 80:20 Wt. Ratio Acetone:H₂O

Methomyl and oxamyl were dissolved in a solvent system consisting of 80 wt. % acetone and 20 wt. % water separately and in 1:1, 2:1 and 1:2.5 wt. ratios of methomyl and oxamyl. These solutions were equilibrated at −6° C and were seeded with methomyl and/or oxamyl. They remained at −6° C until solid-liquid equilibrium was assured. Liquid was removed from each sample at −6° C and assayed for methomyl and oxamyl. Solids were also removed at −6° C, washed, dried and dissolved in methanol to yield a 10 wt. % solution which was evaluated by TLC for oxamyl and methomyl. Both were present in the solids from combination samples. The following results were obtained on the liquids removed from the samples.

SOLUBILITY OF METHOMYL AND OXAMYL 2:1, 1:1 AND 1:2.5 WT. RATIOS IN 80:20 WT ACETONE AND H₂O IN GMS/100 GMS SOLVENT

| Methomyl/Oxamyl ratio | Both Actives in Solvent | | | Methomyl Alone in Solvent gms | Oxamyl Alone in Solvent gms |
|---|---|---|---|---|---|
| | Methomyl gms | Oxamyl gms | Methomyl & Oxamyl gms | | |
| 2:1 | 64.8 | 84.6 | 149.4 | 41.4 | 52.0 |
| 1:1 | 67.0 | 79.3 | 146.3 | 41.4 | 52.0 |
| 1:2.5 | 66.6 | 82.8 | 149.4 | 41.4 | 52.0 |

The data in Examples 2–7 show that increases in solubility occur when oxamyl and methonyl, both active insecticides and nematocides, are dissolved together in the solvents taught. The increases allow significant economies of solvent cost, packaging and shipping by greatly reducing the solvent necessary. The magnitude of these increases is unexpected.

I claim:
1. An insecticidal and nematocidal composition of matter comprising (a) S-methyl-[(methylcarbamoyl)oxy]-thioacetimidate, and (b) methyl N',N'-dimethyl-N-[(methylcarbamoyl)oxy]-1-thiooxamimidate in a solvent, said solvent selected from solvent systems consisting of methanol/water containing from 0 to 70 weight percent water, acetone/water containing from about 0 to 70 weight percent water, and cyclohexanone/cyclohexanol/-methanol/water containing from about 20–92 weight percent cyclohexanone and cyclohexanol provided at least about 35% of this component is cyclohexanone, about 3–25 weight percent methanol and at least about 5 weight percent water, the ratio of (a) to (b) being 2:1 to about 1:2½, said composition having a pH of about 2.8 to 3.2.
2. A composition of claim 1 wherein the solvent system is methanol and water containing from about 0–70 weight percent water.
3. A composition of claim 2 wherein the ratio of (a) to (b) is 1½:1 to 1:1½.
4. The composition of claim 2 further characterized in that it contains sufficient phosphoric acid so as to provide a pH in said range.
5. The composition of claim 2 wherein the ratio of (a) to (b) is about 1:1 to 1:1½.
6. The composition of claim 1 wherein the solvent system is methanol and water containing from about 20–50 weight percent water.
7. The composition of claim 2 wherein a coloring agent is also present.

* * * * *